United States Patent
Kakuta et al.

(10) Patent No.: US 8,026,090 B2
(45) Date of Patent: Sep. 27, 2011

(54) MODIFIED CHONDROITIN SYNTHASE POLYPEPTIDE AND CRYSTAL THEREOF

(75) Inventors: Yoshimitsu Kakuta, Fukuoka (JP); Takuo Osawa, Fukuoka (JP); Nobuo Sugiura, Aichi-gun (JP); Koji Kimata, Aichi-gun (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 13/046,172

(22) Filed: Mar. 11, 2011

(65) Prior Publication Data

US 2011/0195476 A1    Aug. 11, 2011

Related U.S. Application Data

(62) Division of application No. 12/304,487, filed as application No. PCT/JP2007/061789 on Jun. 12, 2007, now Pat. No. 7,927,837.

(30) Foreign Application Priority Data

Jun. 12, 2006   (JP) ................. 2006-162757

(51) Int. Cl.
*C12N 9/10*    (2006.01)
*C12N 1/20*    (2006.01)
*C07H 21/04*    (2006.01)

(52) U.S. Cl. ............... 435/193; 435/252.33; 435/320.1; 536/23.2

(58) Field of Classification Search ................. None
See application file for complete search history.

(56) References Cited

U.S. PATENT DOCUMENTS

2003/0109693 A1    6/2003   Ninomiya et al.

FOREIGN PATENT DOCUMENTS

| EP | 1 283 259 A1 | 2/2003 |
|----|--------------|--------|
| JP | 2003-199583 | 7/2003 |
| WO | WO 2008/133350 A1 | 11/2008 |

OTHER PUBLICATIONS

T. Osawa, et al., "Crystal structure of chondroitin polymerase from *Escherichia coli* strain K4 (K4CP) complexed with UDP-G1cUA and UDP", Protein Data Bank, An Information Portal to Biological Macromolecular Structures, Database PDB [Online], Retreved from: http://www.rcsb org/pdb/explore/explore.do?structureId=2Z86, Database accession No. 2Z86, XP002644108, Sep. 16, 2008, 1 page.

Ninomiya, T. et al., "Molecular Cloning and Characterization of Chondroitin Polymerase from *Escherichia coli* Strain K4*", The Journal of Biological Chemistry, vol. 277, No. 24, pp. 21567-21575, (2002).

Wieneck, J. M. "New Strategies for Protein Crystal Growth", Annu. Rev. Biomed. Eng., 1, pp. 505-534, (1999).

DeAngelis, P. L., "Identification and Molecular Cloning of a Chondroitin Synthase from *Pasteurella multocida* Type F*" The Journal of Biological Chemistry, vol. 275, No. 31, pp. 24124-24129, (2000).

*Primary Examiner* — Nashaat Nashed
(74) *Attorney, Agent, or Firm* — Oblon, Spivak, McClelland, Maier & Neustadt, L.L.P.

(57) ABSTRACT

Disclosed are: (A) a polypeptide consisting of the amino acid sequence of SEQ ID NO:2, or (B) a polypeptide comprising an amino acid sequence of SEQ ID NO:2 including deletion, substitution or addition of one or several amino acid residues and having chondroitin synthase activity; a nucleic acid encoding the polypeptide; a method for producing the polypeptide, comprising at least the steps of: (1) expressing the nucleic acid to produce the polypeptide; and (2) collecting the polypeptide produced in the step (1); and a crystal of the polypeptide. The crystal may be a monoclinic or tetragonal crystal.

12 Claims, 3 Drawing Sheets

{ US 8,026,090 B2 }

MODIFIED CHONDROITIN SYNTHASE POLYPEPTIDE AND CRYSTAL THEREOF

TECHNICAL FIELD

The present invention relates to a modified chondroitin synthase polypeptide, a nucleic acid encoding the polypeptide, a method of producing the polypeptide, a crystal of the polypeptide, and the like.

BACKGROUND ART

Abbreviations, to be used herein and meanings thereof are as follows.
K4CP: Chondroitin synthase derived from *Escherichia coli* K4 strain (serotype O5:K4(L):H4, ATCC 23502)
GalNAc: N-acetyl-D-galactosamine
GlcUA: D-glucuronic acid
SDS: Sodium dodecyl sulfate
SDS-PAGE: Sodium dodecyl sulfate-polyacrylamide gel electrophoresis
UDP: Uridine 5'-diphosphate Patent Document 1 discloses a chondroitin sulfate synthase derived from *Escherichia coli* K4 strain and a DNA encoding the synthase. Patent Document 2 discloses a modified enzyme having a substitution of one or several amino acids in a certain region of K4CP (SEQ ID NO:4).

However, both of the documents do not disclose and suggest the polypeptide of the present invention, nucleic acid encoding the polypeptide, crystal of the polypeptide of the present invention, and the like. In addition, any one of the documents does not disclose and suggest ideas of modifying K4CP (SEQ ID NO:4) to increase the expression level from its DNA, to enhance the enzymatic activity, and to facilitate crystallization.

Patent Document 3 discloses a novel chondroitin sulfate lyase derived from *Proteus vulgaris* and a crystal thereof. However, there is no disclosure or suggestion on K4CP (SEQ ID NO:4).

Patent Document 1: JP 2003-199583 A
Patent Document 2: JP 2005-65565 A
Patent Document 3: JP 10-262660 A

DISCLOSURE OF THE INVENTION

An object of the present invention is to provide: a chondroitin synthase polypeptide which can be expressed at a high level from a nucleic acid, has a high enzymatic activity, and can be crystallized; a nucleic acid encoding the polypeptide; a method of producing the polypeptide; a crystal of the polypeptide; and the like.

The inventors' of the present invention have made extensive studies, and as a result, they have obtained a polypeptide with a deletion in a specific region of K4CP (SEQ ID NO:4) and a nucleic acid encoding the polypeptide. The inventors have surprisingly found that use of the polypeptide as a chondroitin synthase can significantly increase efficiency of the expression from its nucleic acid and can significantly enhance the enzymatic activity and that the peptide can be easily crystallized because the polypeptide molecule is stable, thereby completed the present invention.

That is, the present invention provides a polypeptide represented by the following (A) or (B) (hereinafter, referred to as "polypeptide of the present invention"):

(A) a polypeptide consisting of the amino acid sequence of SEQ ID NO: 2; or
(B) a polypeptide consisting of an amino acid sequence of SEQ ID NO: 2 including deletion, substitution, or addition of one or several amino acids and having chondroitin synthase activity.

In addition, the present invention provides a nucleic acid encoding the polypeptide represented by the following (A) or (B) (hereinafter, referred to as "nucleic acid of the present invention"):

(A) a polypeptide consisting of the amino acid sequence of SEQ ID NO: 2; or
(B) a polypeptide consisting of an amino acid sequence of SEQ ID NO: 2 including deletion, substitution, or addition of one or several amino acids and having chondroitin synthase activity.

As the nucleic acid of the present invention, a nucleic acid as described in the following (a) or (b) may be exemplified:

(a) a DNA consisting of the nucleotide sequence of SEQ ID NO: 1; or
(b) a DNA that hybridizes with a DNA consisting of the nucleotide sequence complementary to the DNA (a) under stringent conditions and has chondroitin synthase activity.

In addition, the present invention provides a method of producing the polypeptide of the present invention, comprising at least the following steps (1) and (2) (hereinafter, referred to as "production method of the present invention"):

(1) a step of expressing a polypeptide from at least one of the nucleic acids of the present invention; and
(2) a step of collecting the polypeptide expressed in the step (1).

In addition, the present invention provides a crystal of the polypeptide of the present invention (hereinafter, referred to as "crystal of the present invention").

As the crystal of the present invention, a plate crystal (hereinafter, referred to as "crystal 1 of the present invention") may be exemplified. Specifically, a crystal showing the following crystal data may be exemplified:
Crystal system: monoclinic system
Bravais lattice: primitive monoclinic lattice
Space group: $P2_1$
Lattice Constant:
a=83.5 Å
b=232.0 Å
c=86.0 Å
β=105.5°

In addition, as the crystal of the present invention, an octahedral crystal (hereinafter, referred to as "crystal 2 of the present invention") may also be exemplified. More specifically, a crystal showing the following crystal data may be exemplified:
Crystal system: tetragonal system
Bravais lattice: primitive tetragonal lattice
Space group: P4
Lattice Constant:
a=336 Å
b=336 Å
c=100 Å

In addition, the present invention provides a method of producing chondroitin comprising reacting a sugar receptor substrate, a D-glucuronic acid donor, and an N-acetyl-D-galactosamine donor in the presence of the polypeptide of the present invention.

BEST MODE FOR CARRYING OUT THE INVENTION

Figure 1:
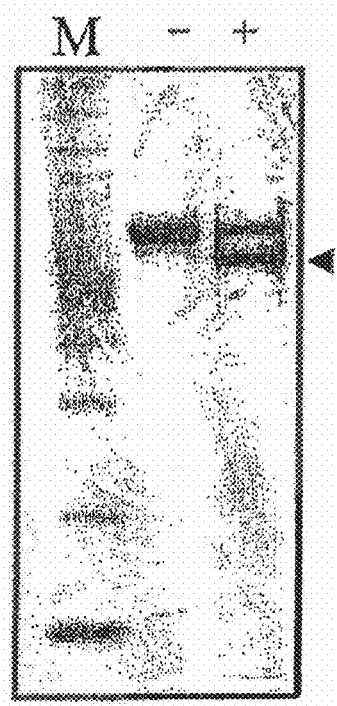
FIG. 1 is a drawing (picture) showing an SDS-PAGE of K4CP (SEQ ID NO:4) treated with trypsin.

Hereinafter, the present invention is described in detail by referring to the best mode for carrying out the invention.

<1> Polypeptide of the Present Invention

The polypeptide of the present invention is a polypeptide represented by the following (A) or (B):

(A) a polypeptide consisting of the amino acid sequence of SEQ ID NO: 2; or (B) a polypeptide consisting of an amino acid sequence of SEQ ID NO: 2 including deletion, substitution, or addition of one or several amino acids and having chondroitin synthase activity.

Hereinafter, explanations are made in order.

Polypeptide (A)

The polypeptide (A) is a K4CP (SEQ ID NO:4) polypeptide in which 57 amino acid residues from the N-terminal are deleted, and the amino acid sequence of the polypeptide is shown in SEQ ID NO: 2. The method of producing the polypeptide is not particularly limited as long as a polypeptide having the sequence can be obtained. For example, the polypeptide can be produced by a peptide synthesis technique, or by removing 57 amino acid residues from the N-terminal with a protease such as trypsin, or by a genetic engineering technique using a nucleic acid encoding the polypeptide. More specific examples are shown in Examples 1 and 2 below. The polypeptide has a high chondroitin synthase activity and can be crystallized easily as described below.

Polypeptide (B)

The polypeptide (B) is a polypeptide consisting of an amino acid sequence of SEQ ID NO: 2 including deletion, substitution, or addition of one or several amino acids and having chondroitin synthase activity.

In a polypeptide, polymorphism or mutation in a nucleic acid encoding the polypeptide may occur, and mutation which causes deletion, substitution, or addition of amino acids may also occur in its amino acid sequence due to the modification of the produced polypeptide in cells and in purification. Despite this, it is known that a certain peptide shows a physiological/biological activity that is substantially equal to that of a polypeptide having no mutation. The polypeptide (B) includes a polypeptide having a structure slightly different from the polypeptide (A) but having no significant difference in the function.

Examples of the addition include addition of one or two or more amino acid residues selected from methionine, alanine, and glycine to the amino terminal of SEQ ID NO: 2 and addition of a peptide sequence for purification or a spacer sequence as described below to the amino terminal or carboxy terminal of SEQ ID NO: 2.

Note that the "amino acid sequence of SEQ ID NO: 2 including addition of one or several amino acids" in (B) does not include the sequence with addition of 57 amino acid residues from the N-terminal of K4CP (SEQ ID NO:4) or a part thereof at the amino terminal of SEQ ID NO: 2, which causes a loss of an expression efficiency and crystallization properties specific to the polypeptide of the present invention.

The term "several amino acids" as used herein refers to the number of amino acid residues that may be mutated as long as the chondroitin synthase activity is not impaired. Specifically, the number is, for example, an integer of 2 to 40, preferably an integer of 2 to 30, more preferably an integer of 2 to 20, still more preferably an integer of 2 to 15, still more preferably an integer of 2 to 10, still more preferably an integer of 2 to 8, and still more preferably an integer of 2 to 6.

The polypeptide of the present invention may have an amino acid sequence having not less than 90%, preferably not less than 95%, more preferably not less than 98% homology to SEQ ID NO: 2 as long as the peptide dose not include 57 amino acid residues from the N-terminal of K4CP (SEQ ID NO:4), and the peptide has chondroitin synthase activity. The homology of amino acid sequences may be determined based on an algorithm by Karlin and Altschul, BLAST (Proc. Natl. Acad. Sci. USA, 90, 5873 (1993)) or FASTA (Methods Enzymol., 183, 63 (1990)).

The polypeptide of the present invention has chondroitin synthase activity. Whether the peptide has the chondroitin synthase activity or not can be verified in accordance with the method described in Example 3 below.

The method of producing the polypeptide is not particularly limited, and the peptide can be produced by a peptide synthesis technique based on an amino acid sequence of SEQ ID NO: 2 including deletion, substitution, or addition of one or several amino acids (having chondroitin synthase activity) or by a genetic engineering technique using a nucleic acid having a mutation introduced therein by the method described below.

The polypeptide of the present invention can be used for synthesis of chondroitin (elongation reaction of chondroitin sugar chain) by contacting the polypeptide with sugar donor substrates (UDP-GalAc and UDP-GluUA) and a sugar receptor substrate (chondroitin oligosaccharide) for the synthesis. In addition, the polypeptide of the present invention can be used as a material for producing the crystal of the present invention to be described below. Details are shown in Examples below.

<2> Nucleic Acid of the Present Invention

The nucleic acid of the present invention is a nucleic acid encoding the following polypeptide (A) or (B):

(A) a polypeptide consisting of the amino acid sequence of SEQ ID NO: 2; or (B) a polypeptide consisting of an amino acid sequence of SEQ ID NO: 2 including deletion, substitution, or addition of one or several amino acids and having chondroitin synthase activity.

The polypeptides (A) and (B) are as described in "<1>Polypeptide of the present invention" above.

The term "nucleic acid" as used herein includes DNA and RNA. Therefore, the kinds of the nucleic acid of the present invention may be DNA or RNA as long as the nucleic acid encodes the aforementioned polypeptide, and in particular, the nucleic acid is preferably a DNA.

A person skilled in the art would easily understand that the nucleic acid of the present invention includes nucleic acids having various nucleotide sequences because of degeneracy of genetic codes.

As the nucleic acid of the present invention, a nucleic acid as described in the following (a) or (b) may be exemplified:

(a) a DNA consisting of the nucleotide sequence of SEQ ID NO: 1; or (b) a DNA that hybridizes with a DNA having the nucleotide sequence complementary to the DNA (a) under stringent conditions and has chondroitin synthase activity.

The term "stringent conditions" as used herein refers to conditions where so-called specific hybrid is formed and non-specific hybrid is not formed (see Sambrook, J. et al., Molecular Cloning A Laboratory Manual, second Edition, Cold Spring Harbor Laboratory Press (1989), etc.). Specific examples of the "stringent conditions" include conditions for hybridization at 42° C. in a solution containing 50% formamide, 4×SSC, 50 mM HEPES (pH 7.0), 10×Denhardt's solution, 100 μg/ml salmon sperm DNA and washing with 2×SSC, 0.1% SDS solution at room temperature and washing with 0.1×SSC, 0.1% SDS solution at 50° C. Whether the polypeptide has chondroitin synthase activity or not can be verified in accordance with the method described in Example 3 below.

The nucleic acid of the present invention has been obtained based on the nucleic acid originally isolated from *Escherichia coli* K4 strain but includes nucleic acids produced by nucleic acid synthesis, genetic engineering technique or the like. As described above, although the method of producing the nucleic acid of the present invention is not particularly limited, the nucleic acid may be produced by the method described in Examples below.

Among the nucleic acids of the present invention, a nucleic acid encoding the polypeptide (B) and the DNA (b) may be produced as follows.

Into the nucleic acid encoding the polypeptide (A) or the DNA (b), deletion, substitution, or addition of nucleotides to cause deletion, substitution, or addition of amino acid residues, which does not substantially impair the chondroitin synthase activity of the polypeptide encoded by such nucleic acids, is introduced. The deletion, substitution, or addition of nucleotides may be introduced into the nucleic acid by synthesizing a sequence which has restriction enzyme-cleavable sites at both ends and contains both side portions of the mutated position, and replacing the corresponding nucleotide sequence contained in the non-mutated nucleic acid with the synthesized sequence. Alternatively, the deletion, substitution, or addition can be also introduced into the nucleic acid in accordance with a method such as site-specific mutagenesis method (Kramer, W. and Frits, H. J., Meth. in Enzymol., 154, 350 (1987); Kunkel, T. A. et al., Meth. in Enzymol., 154, 367 (1987)). If a polypeptide, expressed from a nucleic acid having deletion, substitution, or addition introduced as described above, has chondroitin synthase activity, the nucleic acid can be confirmed to be the nucleic acid of interest. Whether the polypeptide expressed has chondroitin synthase activity or not can be verified in accordance with the method described in Example 3 below.

If the nucleic acid of the present invention, which encodes the polypeptide of the present invention, is expressed, the polypeptide of the present invention can be produced. Details are shown in Examples below.

<3> Production Method of the Present Invention

The production method of the present invention is a method of producing the polypeptide of the present invention including at least the following steps (1) and (2):

(1) a step of expressing the polypeptide from at least one of the nucleic acids of the present invention; and (2) a step of collecting the polypeptide expressed in the step (1).

Hereinafter, explanations are made in order.

The step (1) is a step of expressing a polypeptide from the nucleic acid of the present invention. The nucleic acid of the present invention is as described in "<2> Nucleic acid of the present invention" above.

The method of expressing a polypeptide from the nucleic acid of the present invention is not particularly limited as long as the polypeptide encoded by the nucleic acid of the present invention is produced from the nucleic acid. For example, a polypeptide can be expressed from the nucleic acid of the present invention by: inserting the nucleic acid of the present invention into an appropriate expression vector; introducing the vector into an appropriate host to prepare a transformant, and growing the transformant. The expression vector and host are not particularly limited and may be appropriately selected from known vectors and hosts by a person skilled in the art. Specific examples thereof are shown in Examples below. The term "growing" as used herein includes not only proliferation of cells or microorganisms serving as transformants but also growing of animals, insects; and the like which have been incorporated with the cells serving as transformants. The growth conditions may be appropriately selected by a person skilled in the art depending on the type of a host to be used.

The polypeptide expressed in this step is the polypeptide of the present invention.

The step (2) is a step of collecting the polypeptide (the polypeptide of the present invention) expressed in the step (1).

The method of collecting the polypeptide can be appropriately selected from known methods by a person skilled in the art depending on the expression method of the polypeptide in the step (1).

For example, when the polypeptide of the present invention is expressed and secreted in a medium (the supernatant of the culture broth) by inserting the nucleic acid of the present invention into an expression vector, introducing the vector into a host such as *Escherichia coli*, and culturing the host, the medium may be harvested and used without further treatment as the polypeptide of the present invention.

In addition, when the polypeptide is expressed as a soluble form secreted in the cytoplasm or as an insoluble (membrane-bound) form, the polypeptide expressed may be extracted by a treatment procedure such as: a method using a nitrogen cavitation apparatus; extraction by cell lysis such as homogenization, a glass bead mill method, an ultrasonic disruption method, and an osmotic pressure shock method, or a freezing-thawing method; surfactant extraction; or a combination thereof. Alternatively, the extract may be harvested and used as the polypeptide of the present invention without further treatment.

The production method of the present invention may further include another step as long as the method includes the steps (1) and (2).

For example, a step of purifying the polypeptide of the present invention may be performed after the step (2). Purification may be partial purification or complete purification, and the method may be appropriately selected by a person skilled in the art depending on the purpose of the polypeptide of the present invention or the like.

Specific examples of the purification method include treatment procedures such as salting-out with ammonium sulfate, sodium sulfate, or the like, centrifugation, dialysis, ultrafiltration, adsorption chromatography, ion-exchange chromatography, hydrophobic chromatography, reverse-phase chromatography, gel filtration, gel permeation chromatography; affinity chromatography, electrophoresis, and combination thereof.

The polypeptide of the present invention may be expressed as a fusion protein with other proteins or peptides such as glutathione-S-transferase (GST) or polyhistidine to purify the peptide using an affinity column for the proteins or peptides. Such fusion protein is also included in the polypeptide of the present invention.

Whether the polypeptide of the present invention is produced or not can be confirmed by analyzing the amino acid sequence, functions, and the like of the resultant polypeptide.

<4> Crystal of the Present Invention

The crystal of the present invention is a crystal of the polypeptide of the present invention. That is, the crystal includes the crystals of both the polypeptides (A) and (B) above. The crystal is preferably the crystal of the polypeptide (A).

The crystal of the present invention is not particularly limited as long as the crystal is a product of crystallization of the polypeptide of the present invention. In addition, the method of producing the crystal may be appropriately selected from known techniques used for crystallization of polypeptides by a person skilled in the art. Examples of the crystal of the present invention include monoclinic and tetragonal crystals.

Specific examples of the crystal of the present invention include crystals of the present invention 1 and 2.

The crystal 1 of the present invention is preferably a plate crystal. A crystal showing the following crystal data is more preferred:

Crystal system: monoclinic system
Bravais lattice: primitive monoclinic lattice
Space group: $P2_1$
Lattice Constant:
a=83.5 Å
b=232.0 Å
c=86.0 Å
β=105.5°

The crystal 1 of the present invention can be produced by adding polyethyleneglycol to a solution containing the polypeptide of the present invention at a final concentration of about 15% and allowing the solution to stand at room temperature. More specific production method is as shown in Example '4 below.

The crystal 2 of the present invention is preferably an octahedral crystal. A crystal showing the following crystal data is more preferred:

Crystal system: tetragonal system.
Bravais lattice: primitive tetragonal lattice
Space group: P4
Lattice Constant:
a=336 Å
b=336 Å
c=100 Å

The crystal 2 of the present invention can be produced by adding sodium formate to a solution containing the polypeptide of the present invention at a final concentration of about 4 M and allowing the solution to stand at room temperature. More specific production method is as shown in Example 5 below.

The crystal of the present invention can provide the polypeptide of the present invention at very high purity. For example, crystal of the present invention may be redissolved in an aqueous solvent and used as the polypeptide of the present invention for chondroitin synthesis or the like.

<5> Method of Producing Chondroitin of the Present Invention

The method of producing chondroitin of the present invention includes a step of reacting a sugar receptor substrate, a D-glucuronic acid donor (GlcUA), and an N-acetyl-D-galactosamine donor (GalNAc) in the presence of the polypeptide of the present invention.

The GlcUA donor is preferably nucleoside diphosphate-GlcUA, and particularly preferably UDP-GlcUA. On the other hand, the GalNAc donor is preferably nucleoside diphosphate-GalNAc, particularly preferably UDP-GalNAc.

The sugar receptor substrates are preferably chondroitin, and particularly preferably chondroitin oligosaccharides such as chondroitin tetrasaccharide and chondroitin hexasaccharide. A purified chondroitin can be obtained by producing chondroitin by the above-described reaction and purifying the resultant chondroitin by column chromatography, for example.

The method for producing chondroitin of the present invention is not limited by the molecular weight of the resultant chondroitin, and chondroitin having a molecular weight as high as hundreds of thousands or more can be produced as described in Examples below.

Hereinafter, the present invention is described in detail by referring to the examples.

EXAMPLE 1

Production of polypeptide of the present invention (ΔN57K4CP) (SEQ ID NO:2) by trypsin treatment of wild-type K4CP (SEQ ID NO:4).

A DNA having the nucleotide sequence of SEQ ID NO: 3 (encoding wild-type K4CP (SEQ ID NO:4)) was inserted between a BamHI site (nucleotide numbers 930 to 935 in SEQ ID:NO: 5) and an EcoRI site (nucleotide numbers 938 to 943 in SEQ ID NO: 5) in pGEX4T3 (manufactured by Amersham Biosciences; the nucleotide sequence was shown in SEQ ID NO: 5) as an expression vector. The DNA having the nucleotide sequence of SEQ ID NO: 3 was prepared by the method described in Patent Document 1 ("insert" in Example 2 of Patent Document 1 corresponds to the DNA having the nucleotide sequence of SEQ ID NO: 3).

The DNA was used to transform Escherichia coli Top10F' (Invitrogen), and the polypeptide was expressed in the same way as the method described in Example 2 of Patent Document 1.

The polypeptide expressed by pGEX4T3 was obtained as a fusion protein with GST (glutathione S-transferase), and the polypeptide expressed was subjected to affinity purification using Glutathione Sepharose 4B (GE Healthcare Biosciences).

The purified polypeptide was treated with thrombin to remove GST. The treatment with thrombin was performed by adding 1 unit of thrombin to 13 μg of the polypeptide and incubating the mixture at 4° C. overnight.

After the thrombin treatment, gel filtration (Sephacryl-S200; manufactured by Amersham Biosciences) was performed, to thereby obtain K4CP containing no GST (having the amino acid sequence of SEQ ID NO: 4).

The resultant product was treated with trypsin at a final concentration of 10 ng/ml at 20° C. for 15 minutes. Untreated and treated solutions were subjected to SDS-PAGE (12.5% gel), and the gel was stained with Coomassie brilliant blue. The results are shown in FIG. 1. In FIG. 1, "M", "−", and "+" represent a molecular weight marker, a trypsin-untreated solution, and a trypsin-treated solution, respectively.

As shown in FIG. 1, in the case of the trypsin-treated solution, a band having a slightly smaller molecular weight produced by trypsin treatment (the solid triangle mark in FIG. 1) was detected. As a result of an analysis of an N-terminal amino acid sequence of the band having the smaller molecular weight, the band was found to correspond to a K4CP (SEQ ID NO:4) molecule in which 57 amino acid residues from the N-terminal has been deleted. Therefore, the band was found to be the polypeptide having the amino acid sequence of SEQ ID NO: 2. Hereinafter, the polypeptide is referred to as "ΔN57K4CP" (SEQ ID NO:2).

EXAMPLE 2

Production of the polypeptide of the present invention (ΔN57K4CP) (SEQ ID NO:2) by genetic engineering technique A DNA having the nucleotide sequence of SEQ ID NO: 1 (encoding ΔN57K4CP) (SEQ ID NO:2) was inserted between a BamHI site (nucleotide numbers 930 to 935 in SEQ ID NO: 5) and an EcoRI site (nucleotide numbers 938 to 943 in SEQ ID'NO: 5) in the above-mentioned expression vector, pGEX4T3. The DNA having the nucleotide sequence of SEQ ID NO: 1 was prepared by PCR (polymerase chain reaction).

The DNA was introduced into *Escherichia coli* Top10F' (Invitrogen), and the bacterium was cultured at 30° C. in 2×YT medium supplemented with ampicillin sodium at a final concentration of 100 μg/ml. When the concentration of the bacterial cells in the culture medium (OD600; absorbance at 600 nm) reached 0.6 to 1, IPTG (isopropyl-β-D(−)-thiogalactopyranoside) was added to the culture medium at a final concentration of 0.1 mM, followed by culture at 30° C. overnight. After completion of culture, a supernatant of a cell homogenate was subjected to affinity chromatography using Glutathione Sepharose 4B (GE Healthcare Biosciences).

The purified polypeptide was treated with thrombin to remove GST. The treatment with thrombin was performed in the same way as in Example 1.

Figure 2:
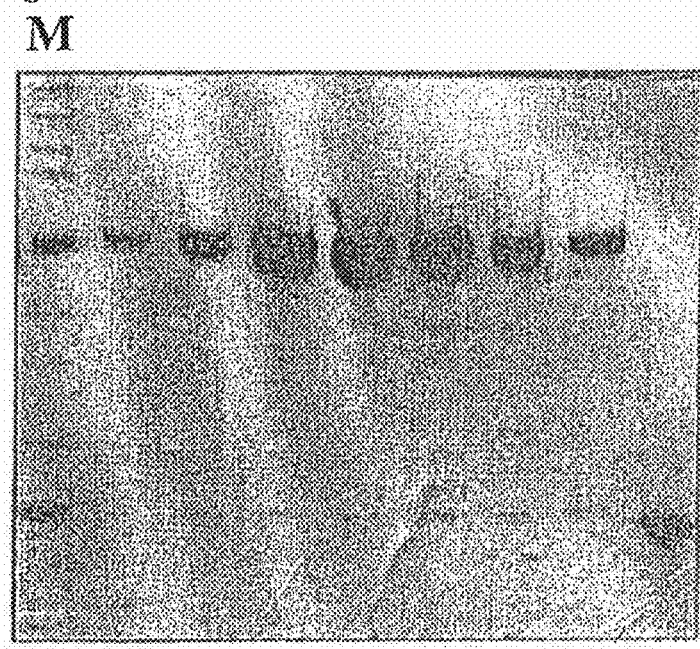
FIG. 2 is a drawing (picture) showing an SDS-PAGE of the fractions of gel filtration chromatography of ΔN57K4CP (SEQ ID NO:2).

After the thrombin treatment, gel filtration was performed in the same way as in Example 1, to thereby obtain ΔN57K4CP (SEQ ID NO:2) containing no GST (having the amino acid sequence of SEQ ID NO: 2). The eluted fractions (7 fractions) obtained by the gel filtration were subjected to SDS-PAGE in the same way as in Example 1, and the gel was stained with Coomassie brilliant blue. The results are shown in FIG. 2. In FIG. 2, "M" represents a molecular weight marker.

FIG. 2 shows that ΔN57K4CP (SEQ ID NO:2) can be produced by the genetic engineering technique. An expression level of ΔN57K4CP (SEQ ID NO:2) expressed in this example was found to be about ten times higher than an expression level of K4CP (SEQ ID NO:4) expressed in Example 1.

EXAMPLE 3

Measurement of Enzymatic Activity

The chondroitin synthase activities of both ΔN57K4CP (SEQ ID NO:2) produced in Example 2 and K4CP (SEQ ID NO:4) produced by the method described in Example 2 of Patent Document 1 (obtained by fusing a peptide containing a His-tag with an N-terminal domain of the polypeptide having the amino acid sequence of SEQ ID NO: 4) were measured. The measurement method is as follows.

A reaction solution (50 μl) containing the polypeptide (2.0 μg) to be measured for its enzymatic activity, 50 mM Tris-HCl (pH 7.2), 20 mM MnCl$_2$, 0.15 M NaCl, chondroitin hexasaccharide (0.1 nmol; Seikagaku Corporation), UDP-[$^3$H]GalNAc (0.1 μCi, 3 nmol), and UDP-GlcUA (3 nmol) was incubated at 30° C. for 30 minutes. After incubation, the reaction solution was heated at 100° C. for one minute to terminate the enzymatic reaction. After that, the solution was applied to Superdex Peptide HR10/30 column (GE Healthcare Biosciences), and gel filtration chromatography was performed using 0.2 M NaCl as an eluent. Fractions containing chondroitin hexasaccharide or larger molecules were collected, and the radioactivity of [$^3$H]GalNAc incorporated by the enzymatic reaction was measured using a scintillation counter.

It was found that the chondroitin synthase activity of ΔN57K4CP (SEQ ID NO:2) was 2.06 times larger than that of K4CP (SEQ ID NO:4).

EXAMPLE 4

Production of Crystal 1 of the Present Invention

Figure 3:
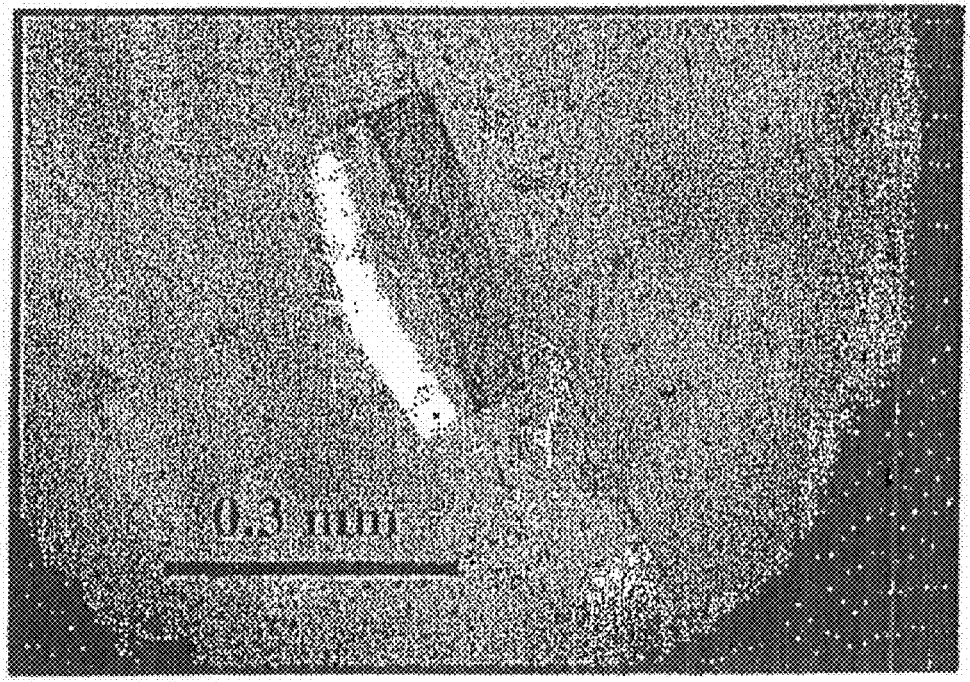
FIG. 3 is a drawing (picture) showing an optical microscope image of crystal 1 of the present invention.

A solution containing ΔN57K4CP (SEQ ID NO:2) obtained in Example 2 at a concentration of 20 mg/ml (solvent composition: 50 mM Tris-HCl (pH 8.0), 500 mM NaCl, 10 mM UDP, and 5 mM MnCl$_2$) was prepared, and polyethyleneglycol (PEG3350; Hampton Research) and NaCl were added to the solution at final concentrations of 15% and 0.2 M, respectively, and the whole was allowed to stand at room temperature. As a result, a crystal of ΔN57K4CP (SEQ ID NO:2) was produced. An optical microscope image of the crystal is shown in FIG. 3. As shown in FIG. 3, the crystal is a plate crystal. X-ray crystallographic analysis was performed for the crystal to obtain the following crystal data.
Crystal system: monoclinic system
Bravais lattice: primitive monoclinic lattice
Space group: P2$_1$
Lattice Constant:
a=83.5 Å
b=232.0 Å
c=86.0 Å
β=105.5°

EXAMPLE 5

Production of Crystal 2 of the Present Invention

Figure 4:
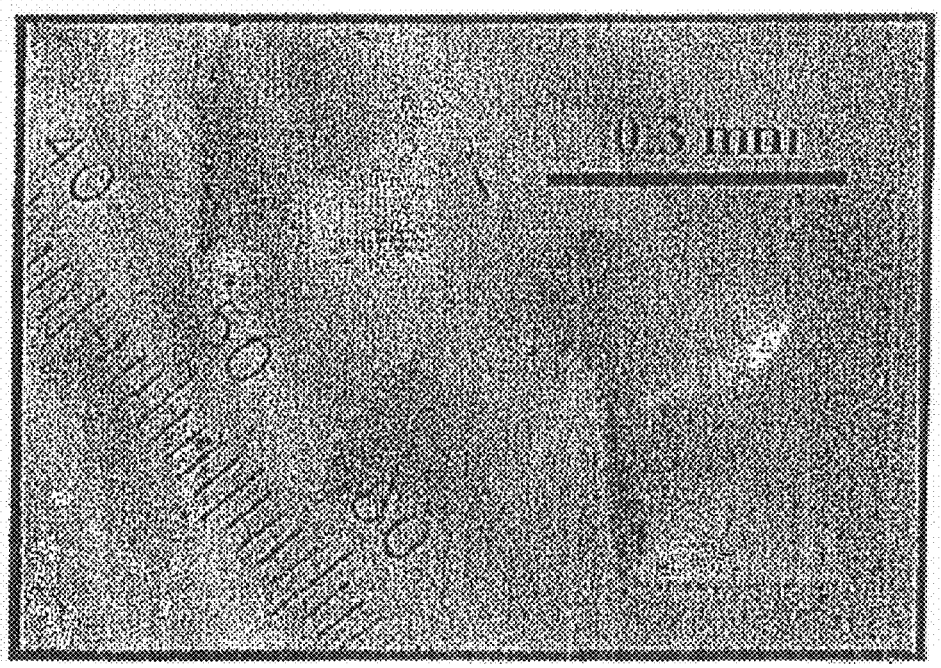
FIG. 4 is a drawing (picture) showing an optical microscope image of crystal 2 of the present invention.

A solution containing ΔN57K4CP (SEQ ID NO:2) obtained in Example 2 at a concentration of 20 mg/ml (solvent composition: 50 mM Tris-HCl (pH 8.0), 50 mM NaCl, 10 mM UDP, and 5 mM MnCl$_2$) was prepared, and sodium formate and dithiothreitol were added to the solution at final concentrations of 4 M and 20 mM, respectively, and the whole was allowed to stand at room temperature. As a result, a crystal of ΔN57K4CP (SEQ ID NO:2) was produced. An optical microscope image of the crystal is shown in FIG. 4. As shown in FIG. 4, the crystal is an octahedral crystal. X-ray crystallographic analysis was performed for the crystal to obtain the following crystal data.
Crystal system: tetragonal system
Bravais lattice: primitive tetragonal lattice
Space group: P4
Lattice Constant:
a=336 Å
b=336 Å
c=100 Å
Although crystallization of K4CP of SEQ ID NO: 4 (where 57 amino acid residues were not removed from the N-terminal) were tried by various methods, but K4CP (SEQ ID NO:4) crystal was not obtained.

EXAMPLE 6

Figure 5:
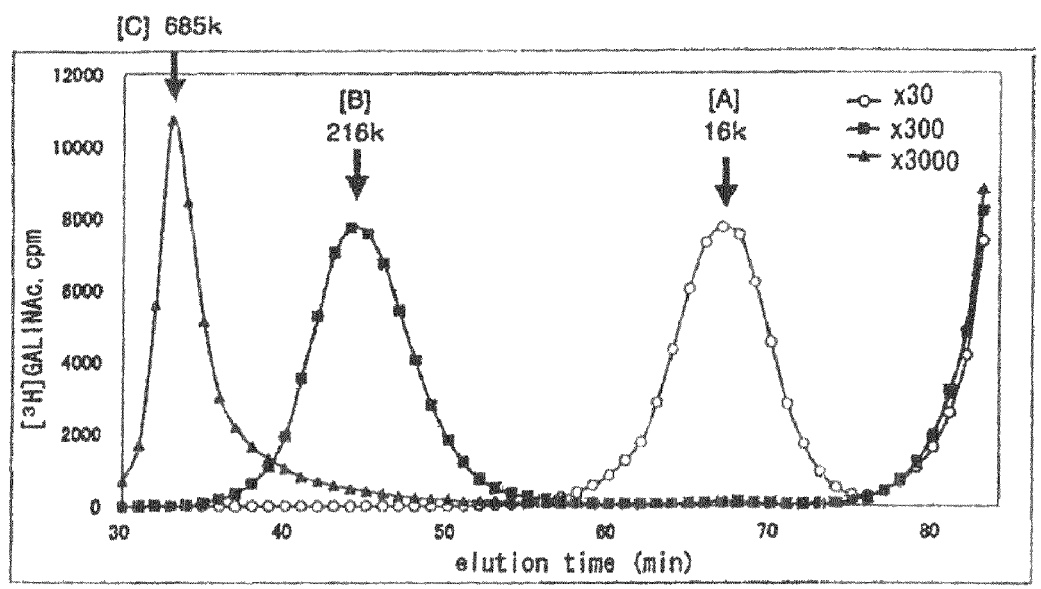
FIG. 5 is a graph showing elution patterns of chondroitins synthesized by using ΔN57K4CP (SEQ ID NO:2).

ΔN57K4CP (SEQ ID NO: 2) (20 μg) produced in Example 2 was incubated in reaction solutions (50 mM Tris-HCl, pH 7.2, 0.2 mM MnCl$_2$, 0.15 M NaCl, 100 µl) containing UDP-[$^3$H]GalNAc (0.1 µCi, 30 nmol), UDP-GlcUA (30 nmol), and chondroitin hexasaccharide ([A] 1 nmol, [B] 0.1 nmol, [C] 0.01 nmol) at 30° C. for 72 hours. The reaction solutions were heated and subjected to gel filtration chromatography at a flow rate of 0.5 ml/min using Sephacryl 5500 HR10/30 column and Superose 6 HR10/30 column (GE Healthcare Biosciences), which were connected in series. [$^3$H] radioactivities of eluted fractions were measured to analyze elution patterns of the synthesized chondroitins (FIG. 5).

A calibration curve of molecular weights was created using a hyaluronic acid reference standard, and average molecular weights of the synthesized chondroitins eluted were calculated based on the calibration curve. As a result, the average molecular weights of [A], [B], and [C] were found to be about 16 kDa, about 216 kDa, and about 685 kDa, respectively.

EXAMPLE 7

ΔN57K4CP (SEQ ID NO:2) (200 µg) produced in Example 2 was incubated in the reaction solutions (100 µl) as used in Example 6 containing UDP-GalNAc having no radioactivity (300 nmol), UDP-GlcUA (300 nmol), and chondroitin hexasaccharide ([A] 10 nmol, [B] 1 nmol, [C] 0.1 nmol) to perform enzymatic reaction. The reaction solutions were heated and applied to Fast Desalting column (GE Healthcare Biosciences), and eluted fractions of higher molecular weights were passed through C18 Sep-Pak (Waters), followed by freeze-drying. Average molecular weights of the resultant synthesized chondroitins in Table 1 shown below, referred to as "rCH") were measured using a multi-angle laser light scattering detector (Wyatt Technology Corporation), and as a result, the molecular weights of [A], [B], and [C] were found to be 34.7 kDa, 157 kDa, and 344 kDa, respectively (Table 1).

TABLE 1

Measurement of molecular weight of rCH by light scattering detector

| Sample name | D/A | First measurement | Second measurement | Average |
|---|---|---|---|---|
| [A] | 30 | 31.8 k | 37.6 k | 34.7 k |
| [B] | 300 | 156 k | 158 k | 157 k |
| [C] | 3,000 | 380 k | 308 k | 344 k |

In this table, "D/A" represents a molar concentration ratio of a sugar-nucleotide donor substrate with respect to chondroitin hexasaccharide. The reaction was performed at 30° C. for 72 hours.

It was found from the results of Examples 6 and 7 that chondroitin having a higher molecular weight can be produced efficiently by using ΔN57K4CP (SEQ ID NO:2).

INDUSTRIAL APPLICABILITY

The polypeptide of the present invention can be used as a tool or the like for producing chondroitin efficiently and inexpensively. It is very useful because the polypeptide can be expressed from a nucleic acid very efficiently compared with wild-type K4CP (SEQ ID NO:4), and it has an enzymatic activity higher than that of wild-type K4CP (SEQ ID NO:4) and can be easily crystallized. Moreover, chondroitin having a higher molecular weight can be produced efficiently by using the polypeptide of the present invention. The nucleic acid of the present invention is very useful because the nucleic acid can be used as a tool for producing the polypeptide of the present invention efficiently and inexpensively. The production method of the present invention is very useful because the method can be used for efficient production of the polypeptide of the present invention. The crystal of the present invention is very useful because the crystal can provide the polypeptide of the preset invention at extremely high purity.

The invention claimed is:

1. An isolated or purified nucleic acid that encodes a polypeptide having chondroitin synthase activity
   (i) that consists of the polypeptide of SEQ ID NO: 2;
   (ii) that consists of the amino acid sequence of SEQ ID NO: 2 except that it includes deletion, substitution, or addition of one or two amino acids within SEQ ID NO: 2;
   (iii) that consists of a polypeptide having no less than 95% homology to the amino acid sequence of SEQ ID NO: 2; or
   (iv) that comprises the amino acid sequence of SEQ ID NO: 2, but which does not include 57 amino acid residues from the N-terminal of K4CP of SEQ ID NO:4.

2. The isolated or purified nucleic acid of claim 1 that encodes a polypeptide having chondroitin synthase activity that consists of the polypeptide of SEQ ID NO: 2.

3. The isolated or purified nucleic acid of claim 1 that encodes a polypeptide that consists of the amino acid sequence of SEQ ID NO: 2 except that it includes deletion, substitution, or addition of one or two amino acids within SEQ ID NO: 2.

4. The isolated or purified nucleic acid of claim 1 that encodes a polypeptide that consists of a polypeptide having no less than 95% homology to the amino acid sequence of SEQ ID NO: 2.

5. The isolated or purified nucleic acid of claim 1 that encodes a polypeptide that consists of a polypeptide having no less than 98% homology to the amino acid sequence of SEQ ID NO: 2.

6. The isolated or purified nucleic acid of claim 1 that encodes a polypeptide comprises the amino acid sequence of SEQ ID NO: 2, but which does not include 57 amino acid residues from the N-terminal of K4CP of SEQ ID NO: 4.

7. The isolated or purified nucleic acid of claim 1 that comprises the nucleotide sequence of SEQ ID NO: 1.

8. The isolated or purified nucleic acid of claim 1 that hybridizes with a DNA consisting of the nucleotide sequence complementary to the polynucleotide sequence of SEQ ID NO: 1 under stringent conditions which comprise washing with 0.1×SSC and 0.1% SDS at a temperature of 50° C.

9. An isolated or purified vector comprising the isolated or purified nucleic acid of claim 1, wherein said vector expresses a polypeptide having chondroitin synthase activity selected from the group consisting of (i) that consists of the polypeptide of SEQ ID NO: 2;
(ii) that consists of the amino acid sequence of SEQ ID NO: 2 except that it includes deletion, substitution, or addition of one or two amino acids within SEQ ID NO: 2;
(iii) that consists of a polypeptide having no less than 95% homology to the amino acid sequence of SEQ ID NO: 2; and
(iv) that comprises the amino acid sequence of SEQ ID NO: 2, but which does not include 57 amino acid residues from the N-terminal of K4CP of SEQ ID NO: 4.

10. A host cell containing the vector of claim 9.

11. A method for producing a polypeptide having chondroitin synthase activity comprising:
culturing the host cell of claim 10.

12. The method of claim 11, further comprising recovering said polypeptide having chrondroitin synthase activity.

* * * * *

SEQUENCE LISTING

```
<160> NUMBER OF SEQ ID NOS: 5

<210> SEQ ID NO 1
<211> LENGTH: 1890
<212> TYPE: DNA
<213> ORGANISM: Artificial sequence
<220> FEATURE:
<223> OTHER INFORMATION: deletion mutant of chondroitin polymerase
      derived from Escherichia coli K4 strain
<220> FEATURE:
<221> NAME/KEY: CDS
<222> LOCATION: (1)..(1890)

<400> SEQUENCE: 1 aaa gct gtt att gat att gat gca gca aca aaa ata atg tgt tct aac        48
Lys Ala Val Ile Asp Ile Asp Ala Ala Thr Lys Ile Met Cys Ser Asn
1               5                   10                  15 gcc aaa gca att agt ctg aac gag gtt gaa aaa aat gaa ata ata agc        96
Ala Lys Ala Ile Ser Leu Asn Glu Val Glu Lys Asn Glu Ile Ile Ser
            20                  25                  30 aaa tac cga gaa ata acc gca aag aaa tca gaa cgg gcg gag tta aag       144
Lys Tyr Arg Glu Ile Thr Ala Lys Lys Ser Glu Arg Ala Glu Leu Lys
        35                  40                  45 gaa gtc gaa ccc att cct tta gat tgg cct agt gat tta act tta ccg       192
Glu Val Glu Pro Ile Pro Leu Asp Trp Pro Ser Asp Leu Thr Leu Pro
    50                  55                  60
```

| | | | | | | | | | | | | | | | | |
|---|---|---|---|---|---|---|---|---|---|---|---|---|---|---|---|---|
| ccg | tta | cct | gag | agc | aca | aac | gat | tat | gtt | tgg | gcg | ggg | aaa | aga | aaa | 240 |
| Pro | Leu | Pro | Glu | Ser | Thr | Asn | Asp | Tyr | Val | Trp | Ala | Gly | Lys | Arg | Lys | |
| 65 | | | | 70 | | | | | 75 | | | | | 80 | | |
| gag | ctt | gat | gat | tat | cca | aga | aaa | cag | tta | atc | att | gac | ggg | ctt | agt | 288 |
| Glu | Leu | Asp | Asp | Tyr | Pro | Arg | Lys | Gln | Leu | Ile | Ile | Asp | Gly | Leu | Ser | |
| | | | | 85 | | | | | 90 | | | | | 95 | | |
| att | gta | att | cct | aca | tat | aat | cga | gca | aaa | ata | ctt | gca | att | aca | ctt | 336 |
| Ile | Val | Ile | Pro | Thr | Tyr | Asn | Arg | Ala | Lys | Ile | Leu | Ala | Ile | Thr | Leu | |
| | | | 100 | | | | | 105 | | | | | 110 | | | |
| gct | tgt | ctt | tgt | aac | caa | aag | acc | ata | tac | gac | tat | gaa | gtt | att | gtt | 384 |
| Ala | Cys | Leu | Cys | Asn | Gln | Lys | Thr | Ile | Tyr | Asp | Tyr | Glu | Val | Ile | Val | |
| | | | 115 | | | | | 120 | | | | | 125 | | | |
| gcc | gat | gat | gga | agt | aaa | gaa | aat | att | gaa | gaa | ata | gta | aga | gaa | ttt | 432 |
| Ala | Asp | Asp | Gly | Ser | Lys | Glu | Asn | Ile | Glu | Glu | Ile | Val | Arg | Glu | Phe | |
| 130 | | | | | 135 | | | | | 140 | | | | | | |
| gaa | agt | tta | tta | aat | ata | aaa | tat | gta | cgt | cag | aag | gat | tat | gga | tat | 480 |
| Glu | Ser | Leu | Leu | Asn | Ile | Lys | Tyr | Val | Arg | Gln | Lys | Asp | Tyr | Gly | Tyr | |
| 145 | | | | | 150 | | | | | 155 | | | | | 160 | |
| caa | ctg | tgt | gct | gtt | aga | aat | ctt | ggg | ctt | agg | gct | gca | aag | tat | aat | 528 |
| Gln | Leu | Cys | Ala | Val | Arg | Asn | Leu | Gly | Leu | Arg | Ala | Ala | Lys | Tyr | Asn | |
| | | | | 165 | | | | | 170 | | | | | 175 | | |
| tat | gtt | gca | att | ctg | gat | tgt | gat | atg | gct | ccg | aac | cca | cta | tgg | gtt | 576 |
| Tyr | Val | Ala | Ile | Leu | Asp | Cys | Asp | Met | Ala | Pro | Asn | Pro | Leu | Trp | Val | |
| | | | 180 | | | | | 185 | | | | | 190 | | | |
| cag | tca | tat | atg | gaa | cta | tta | gcg | gtg | gac | gat | aat | gtt | gct | cta | att | 624 |
| Gln | Ser | Tyr | Met | Glu | Leu | Leu | Ala | Val | Asp | Asp | Asn | Val | Ala | Leu | Ile | |
| | | | 195 | | | | | 200 | | | | | 205 | | | |
| ggc | cct | aga | aaa | tat | ata | gat | aca | agc | aag | cat | aca | tat | tta | gat | ttc | 672 |
| Gly | Pro | Arg | Lys | Tyr | Ile | Asp | Thr | Ser | Lys | His | Thr | Tyr | Leu | Asp | Phe | |
| 210 | | | | | 215 | | | | | 220 | | | | | | |
| ctt | tcc | caa | aaa | tca | cta | ata | aat | gaa | att | cct | gaa | atc | att | act | aat | 720 |
| Leu | Ser | Gln | Lys | Ser | Leu | Ile | Asn | Glu | Ile | Pro | Glu | Ile | Ile | Thr | Asn | |
| 225 | | | | | 230 | | | | | 235 | | | | | 240 | |
| aat | cag | gtt | gca | ggc | aag | gtt | gag | caa | aac | aaa | tca | gtt | gac | tgg | cga | 768 |
| Asn | Gln | Val | Ala | Gly | Lys | Val | Glu | Gln | Asn | Lys | Ser | Val | Asp | Trp | Arg | |
| | | | | 245 | | | | | 250 | | | | | 255 | | |
| ata | gaa | cat | ttc | aaa | aat | acc | gat | aat | cta | aga | tta | tgc | aac | aca | cca | 816 |
| Ile | Glu | His | Phe | Lys | Asn | Thr | Asp | Asn | Leu | Arg | Leu | Cys | Asn | Thr | Pro | |
| | | | 260 | | | | | 265 | | | | | 270 | | | |
| ttt | cga | ttt | ttt | agc | gga | ggt | aat | gtc | gct | ttt | gcg | aaa | aaa | tgg | ctt | 864 |
| Phe | Arg | Phe | Phe | Ser | Gly | Gly | Asn | Val | Ala | Phe | Ala | Lys | Lys | Trp | Leu | |
| | | | 275 | | | | | 280 | | | | | 285 | | | |
| ttc | cgt | gca | gga | tgg | ttt | gat | gaa | gag | ttt | acg | cat | tgg | ggg | ggg | gag | 912 |
| Phe | Arg | Ala | Gly | Trp | Phe | Asp | Glu | Glu | Phe | Thr | His | Trp | Gly | Gly | Glu | |
| | | 290 | | | | | 295 | | | | | 300 | | | | |
| gat | aat | gag | ttt | gga | tat | cgt | ctc | tac | aga | gaa | gga | tgt | tac | ttt | cgg | 960 |
| Asp | Asn | Glu | Phe | Gly | Tyr | Arg | Leu | Tyr | Arg | Glu | Gly | Cys | Tyr | Phe | Arg | |
| 305 | | | | 310 | | | | | 315 | | | | | 320 | | |
| tct | gtt | gaa | gga | gca | atg | gca | tat | cat | caa | gaa | cca | ccc | ggg | aaa | gaa | 1008 |
| Ser | Val | Glu | Gly | Ala | Met | Ala | Tyr | His | Gln | Glu | Pro | Pro | Gly | Lys | Glu | |
| | | | | 325 | | | | | 330 | | | | | 335 | | |
| aac | gag | acg | gat | cgt | gcg | gca | ggg | aaa | aat | att | act | gtt | caa | ttg | tta | 1056 |
| Asn | Glu | Thr | Asp | Arg | Ala | Ala | Gly | Lys | Asn | Ile | Thr | Val | Gln | Leu | Leu | |
| | | | 340 | | | | | 345 | | | | | 350 | | | |
| cag | caa | aaa | gtt | cct | tat | ttc | tat | aga | aaa | aaa | gaa | aaa | ata | gaa | tcc | 1104 |
| Gln | Gln | Lys | Val | Pro | Tyr | Phe | Tyr | Arg | Lys | Lys | Glu | Lys | Ile | Glu | Ser | |
| | | 355 | | | | | 360 | | | | | 365 | | | | |
| gcg | aca | tta | aaa | aga | gta | cca | cta | gta | tct | ata | tat | att | ccc | gcc | tat | 1152 |
| Ala | Thr | Leu | Lys | Arg | Val | Pro | Leu | Val | Ser | Ile | Tyr | Ile | Pro | Ala | Tyr | |
| 370 | | | | | 375 | | | | | 380 | | | | | | |

-continued

```
aac tgc tct aaa tat att gtt cgt tgt gtt gaa agc gcc ctt aat cag    1200
Asn Cys Ser Lys Tyr Ile Val Arg Cys Val Glu Ser Ala Leu Asn Gln
385                 390                 395                 400 aca ata act gac tta gaa gta tgc ata tgc gat gat ggt tcc aca gat    1248
Thr Ile Thr Asp Leu Glu Val Cys Ile Cys Asp Asp Gly Ser Thr Asp
            405                 410                 415 gat aca ttg cgg att ctt cag gag cat tat gca aac cat cct cga gtt    1296
Asp Thr Leu Arg Ile Leu Gln Glu His Tyr Ala Asn His Pro Arg Val
        420                 425                 430 cgt ttt att tca caa aaa aac aaa gga att ggt tca gca tct aat aca    1344
Arg Phe Ile Ser Gln Lys Asn Lys Gly Ile Gly Ser Ala Ser Asn Thr
    435                 440                 445 gca gtt aga ttg tgt cgg gga ttc tat ata ggt cag tta gac tct gat    1392
Ala Val Arg Leu Cys Arg Gly Phe Tyr Ile Gly Gln Leu Asp Ser Asp
450                 455                 460 gac ttt ctt gaa cca gat gct gtt gaa cta tgt cta gat gaa ttt aga    1440
Asp Phe Leu Glu Pro Asp Ala Val Glu Leu Cys Leu Asp Glu Phe Arg
465                 470                 475                 480 aaa gat cta tca ttg gca tgt gtt tat aca act aac cgt aat ata gat    1488
Lys Asp Leu Ser Leu Ala Cys Val Tyr Thr Thr Asn Arg Asn Ile Asp
            485                 490                 495 cgt gaa ggt aat ttg ata tca aat ggc tat aat tgg ccc att tat tcg    1536
Arg Glu Gly Asn Leu Ile Ser Asn Gly Tyr Asn Trp Pro Ile Tyr Ser
        500                 505                 510 cga gaa aaa ctt act agt gca atg ata tgt cat cat ttc agg atg ttc    1584
Arg Glu Lys Leu Thr Ser Ala Met Ile Cys His His Phe Arg Met Phe
    515                 520                 525 aca gca aga gca tgg aac cta act gaa ggt ttc aac gaa tcg atc agc    1632
Thr Ala Arg Ala Trp Asn Leu Thr Glu Gly Phe Asn Glu Ser Ile Ser
530                 535                 540 aac gca gtt gat tac gat atg tat tta aaa ctt agt gaa gtt gga ccg    1680
Asn Ala Val Asp Tyr Asp Met Tyr Leu Lys Leu Ser Glu Val Gly Pro
545                 550                 555                 560 ttc aag cat ata aac aaa att tgt tat aat cgc gta ttg cat ggt gaa    1728
Phe Lys His Ile Asn Lys Ile Cys Tyr Asn Arg Val Leu His Gly Glu
            565                 570                 575 aat acg tct ata aaa aag ttg gat att caa aag gaa aat cat ttt aaa    1776
Asn Thr Ser Ile Lys Lys Leu Asp Ile Gln Lys Glu Asn His Phe Lys
        580                 585                 590 gtt gtt aac gaa tca tta agt agg cta ggc ata aaa aaa tat aaa tat    1824
Val Val Asn Glu Ser Leu Ser Arg Leu Gly Ile Lys Lys Tyr Lys Tyr
    595                 600                 605 tca cca tta act aat ttg aat gaa tgt aga aaa tat acc tgg gaa aaa    1872
Ser Pro Leu Thr Asn Leu Asn Glu Cys Arg Lys Tyr Thr Trp Glu Lys
610                 615                 620 ata gag aat gat tta taa                                            1890
Ile Glu Asn Asp Leu
625

<210> SEQ ID NO 2
<211> LENGTH: 629
<212> TYPE: PRT
<213> ORGANISM: Artificial sequence
<220> FEATURE:
<223> OTHER INFORMATION: Synthetic Construct

<400> SEQUENCE: 2

Lys Ala Val Ile Asp Ile Asp Ala Ala Thr Lys Ile Met Cys Ser Asn
1               5                   10                  15

Ala Lys Ala Ile Ser Leu Asn Glu Val Glu Lys Asn Glu Ile Ile Ser
            20                  25                  30
```

-continued

```
Lys Tyr Arg Glu Ile Thr Ala Lys Ser Glu Arg Ala Glu Leu Lys
             35                  40                  45
Glu Val Glu Pro Ile Pro Leu Asp Trp Pro Ser Asp Leu Thr Leu Pro
 50                  55                  60
Pro Leu Pro Glu Ser Thr Asn Asp Tyr Val Trp Ala Gly Lys Arg Lys
 65                  70                  75                  80
Glu Leu Asp Asp Tyr Pro Arg Lys Gln Leu Ile Ile Asp Gly Leu Ser
                 85                  90                  95
Ile Val Ile Pro Thr Tyr Asn Arg Ala Lys Ile Leu Ala Ile Thr Leu
                100                 105                 110
Ala Cys Leu Cys Asn Gln Lys Thr Ile Tyr Asp Tyr Glu Val Ile Val
            115                 120                 125
Ala Asp Asp Gly Ser Lys Glu Asn Ile Glu Ile Val Arg Glu Phe
            130                 135                 140
Glu Ser Leu Leu Asn Ile Lys Tyr Val Arg Gln Lys Asp Tyr Gly Tyr
145                 150                 155                 160
Gln Leu Cys Ala Val Arg Asn Leu Gly Leu Arg Ala Ala Lys Tyr Asn
                165                 170                 175
Tyr Val Ala Ile Leu Asp Cys Asp Met Ala Pro Asn Pro Leu Trp Val
            180                 185                 190
Gln Ser Tyr Met Glu Leu Leu Ala Val Asp Asp Asn Val Ala Leu Ile
            195                 200                 205
Gly Pro Arg Lys Tyr Ile Asp Thr Ser Lys His Thr Tyr Leu Asp Phe
            210                 215                 220
Leu Ser Gln Lys Ser Leu Ile Asn Glu Ile Pro Glu Ile Ile Thr Asn
225                 230                 235                 240
Asn Gln Val Ala Gly Lys Val Glu Gln Asn Lys Ser Val Asp Trp Arg
                245                 250                 255
Ile Glu His Phe Lys Asn Thr Asp Asn Leu Arg Leu Cys Asn Thr Pro
            260                 265                 270
Phe Arg Phe Phe Ser Gly Gly Asn Val Ala Phe Ala Lys Lys Trp Leu
            275                 280                 285
Phe Arg Ala Gly Trp Phe Asp Glu Glu Phe Thr His Trp Gly Gly Glu
            290                 295                 300
Asp Asn Glu Phe Gly Tyr Arg Leu Tyr Arg Glu Gly Cys Tyr Phe Arg
305                 310                 315                 320
Ser Val Glu Gly Ala Met Ala Tyr His Gln Glu Pro Pro Gly Lys Glu
                325                 330                 335
Asn Glu Thr Asp Arg Ala Ala Gly Lys Asn Ile Thr Val Gln Leu Leu
            340                 345                 350
Gln Gln Lys Val Pro Tyr Phe Tyr Arg Lys Glu Lys Ile Glu Ser
            355                 360                 365
Ala Thr Leu Lys Arg Val Pro Leu Val Ser Ile Tyr Ile Pro Ala Tyr
            370                 375                 380
Asn Cys Ser Lys Tyr Ile Val Arg Cys Val Glu Ser Ala Leu Asn Gln
385                 390                 395                 400
Thr Ile Thr Asp Leu Glu Val Cys Ile Cys Asp Asp Gly Ser Thr Asp
                405                 410                 415
Asp Thr Leu Arg Ile Leu Gln Glu His Tyr Ala Asn His Pro Arg Val
            420                 425                 430
Arg Phe Ile Ser Gln Lys Asn Lys Gly Ile Gly Ser Ala Ser Asn Thr
            435                 440                 445
Ala Val Arg Leu Cys Arg Gly Phe Tyr Ile Gly Gln Leu Asp Ser Asp
```

```
                450             455             460
Asp Phe Leu Glu Pro Asp Ala Val Glu Leu Cys Leu Asp Glu Phe Arg
465                 470                 475                 480

Lys Asp Leu Ser Leu Ala Cys Val Tyr Thr Thr Asn Arg Asn Ile Asp
                485                 490                 495

Arg Glu Gly Asn Leu Ile Ser Asn Gly Tyr Asn Trp Pro Ile Tyr Ser
            500                 505                 510

Arg Glu Lys Leu Thr Ser Ala Met Ile Cys His His Phe Arg Met Phe
        515                 520                 525

Thr Ala Arg Ala Trp Asn Leu Thr Gly Phe Asn Glu Ser Ile Ser
    530                 535                 540

Asn Ala Val Asp Tyr Asp Met Tyr Leu Lys Leu Ser Glu Val Gly Pro
545                 550                 555                 560

Phe Lys His Ile Asn Lys Ile Cys Tyr Asn Arg Val Leu His Gly Glu
                565                 570                 575

Asn Thr Ser Ile Lys Lys Leu Asp Ile Gln Lys Glu Asn His Phe Lys
            580                 585                 590

Val Val Asn Glu Ser Leu Ser Arg Leu Gly Ile Lys Lys Tyr Lys Tyr
        595                 600                 605

Ser Pro Leu Thr Asn Leu Asn Glu Cys Arg Lys Tyr Thr Trp Glu Lys
    610                 615                 620

Ile Glu Asn Asp Leu
625

<210> SEQ ID NO 3
<211> LENGTH: 2058
<212> TYPE: DNA
<213> ORGANISM: Escherichia coli
<220> FEATURE:
<221> NAME/KEY: CDS
<222> LOCATION: (1)..(2058)

<400> SEQUENCE: 3 atg agt att ctt aat caa gca ata aat tta tat aaa aac aaa aat tat     48
Met Ser Ile Leu Asn Gln Ala Ile Asn Leu Tyr Lys Asn Lys Asn Tyr
1               5                   10                  15 cgc caa gct tta tct ctt ttt gag aag gtt gct gaa att tat gat gtt     96
Arg Gln Ala Leu Ser Leu Phe Glu Lys Val Ala Glu Ile Tyr Asp Val
            20                  25                  30 agt tgg gtc gaa gca aat ata aaa tta tgc caa acc gca ctc aat ctt    144
Ser Trp Val Glu Ala Asn Ile Lys Leu Cys Gln Thr Ala Leu Asn Leu
        35                  40                  45 tct gaa gaa gtt gat aag tta aat cgt aaa gct gtt att gat att gat    192
Ser Glu Glu Val Asp Lys Leu Asn Arg Lys Ala Val Ile Asp Ile Asp
    50                  55                  60 gca gca aca aaa ata atg tgt tct aac gcc aaa gca att agt ctg aac    240
Ala Ala Thr Lys Ile Met Cys Ser Asn Ala Lys Ala Ile Ser Leu Asn
65                  70                  75                  80 gag gtt gaa aaa aat gaa ata ata agc aaa tac cga gaa ata acc gca    288
Glu Val Glu Lys Asn Glu Ile Ile Ser Lys Tyr Arg Glu Ile Thr Ala
                85                  90                  95 aag aaa tca gaa cgg gcg gag tta aag gaa gtc gaa ccc att cct tta    336
Lys Lys Ser Glu Arg Ala Glu Leu Lys Glu Val Glu Pro Ile Pro Leu
            100                 105                 110 gat tgg cct agt gat tta act tta ccg ccg tta cct gag agc aca aac    384
Asp Trp Pro Ser Asp Leu Thr Leu Pro Pro Leu Pro Glu Ser Thr Asn
        115                 120                 125 gat tat gtt tgg gcg ggg aaa aga aaa gag ctt gat gat tat cca aga    432
Asp Tyr Val Trp Ala Gly Lys Arg Lys Glu Leu Asp Asp Tyr Pro Arg
```

-continued

```
            130                 135                 140
aaa cag tta atc att gac ggg ctt agt att gta att cct aca tat aat      480
Lys Gln Leu Ile Ile Asp Gly Leu Ser Ile Val Ile Pro Thr Tyr Asn
145                 150                 155                 160 cga gca aaa ata ctt gca att aca ctt gct tgt ctt tgt aac caa aag      528
Arg Ala Lys Ile Leu Ala Ile Thr Leu Ala Cys Leu Cys Asn Gln Lys
                165                 170                 175 acc ata tac gac tat gaa gtt att gtt gcc gat gat gga agt aaa gaa      576
Thr Ile Tyr Asp Tyr Glu Val Ile Val Ala Asp Asp Gly Ser Lys Glu
            180                 185                 190 aat att gaa gaa ata gta aga gaa ttt gaa agt tta tta aat ata aaa      624
Asn Ile Glu Glu Ile Val Arg Glu Phe Glu Ser Leu Leu Asn Ile Lys
        195                 200                 205 tat gta cgt cag aag gat tat gga tat caa ctg tgt gct gtt aga aat      672
Tyr Val Arg Gln Lys Asp Tyr Gly Tyr Gln Leu Cys Ala Val Arg Asn
    210                 215                 220 ctt ggg ctt agg gct gca aag tat aat tat gtt gca att ctg gat tgt      720
Leu Gly Leu Arg Ala Ala Lys Tyr Asn Tyr Val Ala Ile Leu Asp Cys
225                 230                 235                 240 gat atg gct ccg aac cca cta tgg gtt cag tca tat atg gaa cta tta      768
Asp Met Ala Pro Asn Pro Leu Trp Val Gln Ser Tyr Met Glu Leu Leu
                245                 250                 255 gcg gtg gac gat aat gtt gct cta att ggc cct aga aaa tat ata gat      816
Ala Val Asp Asp Asn Val Ala Leu Ile Gly Pro Arg Lys Tyr Ile Asp
            260                 265                 270 aca agc aag cat aca tat tta gat ttc ctt tcc caa aaa tca cta ata      864
Thr Ser Lys His Thr Tyr Leu Asp Phe Leu Ser Gln Lys Ser Leu Ile
        275                 280                 285 aat gaa att cct gaa atc att act aat aat cag gtt gca ggc aag gtt      912
Asn Glu Ile Pro Glu Ile Ile Thr Asn Asn Gln Val Ala Gly Lys Val
    290                 295                 300 gag caa aac aaa tca gtt gac tgg cga ata gaa cat ttc aaa aat acc      960
Glu Gln Asn Lys Ser Val Asp Trp Arg Ile Glu His Phe Lys Asn Thr
305                 310                 315                 320 gat aat cta aga tta tgc aac aca cca ttt cga ttt ttt agc gga ggt     1008
Asp Asn Leu Arg Leu Cys Asn Thr Pro Phe Arg Phe Phe Ser Gly Gly
                325                 330                 335 aat gtc gct ttt gcg aaa aaa tgg ctt ttc cgt gca gga tgg ttt gat     1056
Asn Val Ala Phe Ala Lys Lys Trp Leu Phe Arg Ala Gly Trp Phe Asp
            340                 345                 350 gaa gag ttt acg cat tgg ggg ggg gag gat aat gag ttt gga tat cgt     1104
Glu Glu Phe Thr His Trp Gly Gly Glu Asp Asn Glu Phe Gly Tyr Arg
        355                 360                 365 ctc tac aga gaa gga tgt tac ttt cgg tct gtt gaa gga gca atg gca     1152
Leu Tyr Arg Glu Gly Cys Tyr Phe Arg Ser Val Glu Gly Ala Met Ala
    370                 375                 380 tat cat caa gaa cca ccc ggg aaa gaa aac gag acg gat cgt gcg gca     1200
Tyr His Gln Glu Pro Pro Gly Lys Glu Asn Glu Thr Asp Arg Ala Ala
385                 390                 395                 400 ggg aaa aat att act gtt caa ttg tta cag caa aaa gtt cct tat ttc     1248
Gly Lys Asn Ile Thr Val Gln Leu Leu Gln Gln Lys Val Pro Tyr Phe
                405                 410                 415 tat aga aaa aaa gaa aaa ata gaa tcc gcg aca tta aaa aga gta cca     1296
Tyr Arg Lys Lys Glu Lys Ile Glu Ser Ala Thr Leu Lys Arg Val Pro
            420                 425                 430 cta gta tct ata tat att ccc gcc tat aac tgc tct aaa tat att gtt     1344
Leu Val Ser Ile Tyr Ile Pro Ala Tyr Asn Cys Ser Lys Tyr Ile Val
        435                 440                 445 cgt tgt gtt gaa agc gcc ctt aat cag aca ata act gac tta gaa gta     1392
Arg Cys Val Glu Ser Ala Leu Asn Gln Thr Ile Thr Asp Leu Glu Val
```

```
               450                 455                 460
tgc ata tgc gat gat ggt tcc aca gat gat aca ttg cgg att ctt cag         1440
Cys Ile Cys Asp Asp Gly Ser Thr Asp Asp Thr Leu Arg Ile Leu Gln
465                 470                 475                 480 gag cat tat gca aac cat cct cga gtt cgt ttt att tca caa aaa aac         1488
Glu His Tyr Ala Asn His Pro Arg Val Arg Phe Ile Ser Gln Lys Asn
                485                 490                 495 aaa gga att ggt tca gca tct aat aca gca gtt aga ttg tgt cgg gga         1536
Lys Gly Ile Gly Ser Ala Ser Asn Thr Ala Val Arg Leu Cys Arg Gly
            500                 505                 510 ttc tat ata ggt cag tta gac tct gat gac ttt ctt gaa cca gat gct         1584
Phe Tyr Ile Gly Gln Leu Asp Ser Asp Asp Phe Leu Glu Pro Asp Ala
        515                 520                 525 gtt gaa cta tgt cta gat gaa ttt aga aaa gat cta tca ttg gca tgt         1632
Val Glu Leu Cys Leu Asp Glu Phe Arg Lys Asp Leu Ser Leu Ala Cys
    530                 535                 540 gtt tat aca act aac cgt aat ata gat cgt gaa ggt aat ttg ata tca         1680
Val Tyr Thr Thr Asn Arg Asn Ile Asp Arg Glu Gly Asn Leu Ile Ser
545                 550                 555                 560 aat ggc tat aat tgg ccc att tat tcg cga gaa aaa ctt act agt gca         1728
Asn Gly Tyr Asn Trp Pro Ile Tyr Ser Arg Glu Lys Leu Thr Ser Ala
                565                 570                 575 atg ata tgt cat cat ttc agg atg ttc aca gca aga gca tgg aac cta         1776
Met Ile Cys His His Phe Arg Met Phe Thr Ala Arg Ala Trp Asn Leu
            580                 585                 590 act gaa ggt ttc aac gaa tcg atc agc aac gca gtt gat tac gat atg         1824
Thr Glu Gly Phe Asn Glu Ser Ile Ser Asn Ala Val Asp Tyr Asp Met
        595                 600                 605 tat tta aaa ctt agt gaa gtt gga ccg ttc aag cat ata aac aaa att         1872
Tyr Leu Lys Leu Ser Glu Val Gly Pro Phe Lys His Ile Asn Lys Ile
    610                 615                 620 tgt tat aat cgc gta ttg cat ggt gaa aat acg tct ata aaa aag ttg         1920
Cys Tyr Asn Arg Val Leu His Gly Glu Asn Thr Ser Ile Lys Lys Leu
625                 630                 635                 640 gat att caa aag gaa aat cat ttt aaa gtt gtt aac gaa tca tta agt         1968
Asp Ile Gln Lys Glu Asn His Phe Lys Val Val Asn Glu Ser Leu Ser
                645                 650                 655 agg cta ggc ata aaa aaa tat aaa tat tca cca tta act aat ttg aat         2016
Arg Leu Gly Ile Lys Lys Tyr Lys Tyr Ser Pro Leu Thr Asn Leu Asn
            660                 665                 670 gaa tgt aga aaa tat acc tgg gaa aaa ata gag aat gat tta                 2058
Glu Cys Arg Lys Tyr Thr Trp Glu Lys Ile Glu Asn Asp Leu
        675                 680                 685

<210> SEQ ID NO 4
<211> LENGTH: 686
<212> TYPE: PRT
<213> ORGANISM: Escherichia coli

<400> SEQUENCE: 4

Met Ser Ile Leu Asn Gln Ala Ile Asn Leu Tyr Lys Asn Lys Asn Tyr
1               5                   10                  15

Arg Gln Ala Leu Ser Leu Phe Glu Lys Val Ala Glu Ile Tyr Asp Val
            20                  25                  30

Ser Trp Val Glu Ala Asn Ile Lys Leu Cys Gln Thr Ala Leu Asn Leu
        35                  40                  45

Ser Glu Glu Val Asp Lys Leu Asn Arg Lys Ala Val Ile Asp Ile Asp
    50                  55                  60

Ala Ala Thr Lys Ile Met Cys Ser Asn Ala Lys Ala Ile Ser Leu Asn
65                  70                  75                  80
```

-continued

```
Glu Val Glu Lys Asn Glu Ile Ile Ser Lys Tyr Arg Glu Ile Thr Ala
                85                  90                  95
Lys Lys Ser Glu Arg Ala Glu Leu Lys Glu Val Glu Pro Ile Pro Leu
            100                 105                 110
Asp Trp Pro Ser Asp Leu Thr Leu Pro Pro Leu Pro Glu Ser Thr Asn
        115                 120                 125
Asp Tyr Val Trp Ala Gly Lys Arg Lys Glu Leu Asp Asp Tyr Pro Arg
    130                 135                 140
Lys Gln Leu Ile Ile Asp Gly Leu Ser Ile Val Ile Pro Thr Tyr Asn
145                 150                 155                 160
Arg Ala Lys Ile Leu Ala Ile Thr Leu Ala Cys Leu Cys Asn Gln Lys
                165                 170                 175
Thr Ile Tyr Asp Tyr Glu Val Ile Val Ala Asp Asp Gly Ser Lys Glu
            180                 185                 190
Asn Ile Glu Glu Ile Val Arg Glu Phe Glu Ser Leu Leu Asn Ile Lys
        195                 200                 205
Tyr Val Arg Gln Lys Asp Tyr Gly Tyr Gln Leu Cys Ala Val Arg Asn
    210                 215                 220
Leu Gly Leu Arg Ala Ala Lys Tyr Asn Tyr Val Ala Ile Leu Asp Cys
225                 230                 235                 240
Asp Met Ala Pro Asn Pro Leu Trp Val Gln Ser Tyr Met Glu Leu Leu
                245                 250                 255
Ala Val Asp Asp Asn Val Ala Leu Ile Gly Pro Arg Lys Tyr Ile Asp
            260                 265                 270
Thr Ser Lys His Thr Tyr Leu Asp Phe Leu Ser Gln Lys Ser Leu Ile
        275                 280                 285
Asn Glu Ile Pro Glu Ile Ile Thr Asn Asn Gln Val Ala Gly Lys Val
    290                 295                 300
Glu Gln Asn Lys Ser Val Asp Trp Arg Ile Glu His Phe Lys Asn Thr
305                 310                 315                 320
Asp Asn Leu Arg Leu Cys Asn Thr Pro Phe Arg Phe Ser Gly Gly
                325                 330                 335
Asn Val Ala Phe Ala Lys Lys Trp Leu Phe Arg Ala Gly Trp Phe Asp
            340                 345                 350
Glu Glu Phe Thr His Trp Gly Gly Glu Asp Asn Glu Phe Gly Tyr Arg
        355                 360                 365
Leu Tyr Arg Glu Gly Cys Tyr Phe Arg Ser Val Glu Gly Ala Met Ala
    370                 375                 380
Tyr His Gln Glu Pro Pro Gly Lys Glu Asn Glu Thr Asp Arg Ala Ala
385                 390                 395                 400
Gly Lys Asn Ile Thr Val Gln Leu Leu Gln Gln Lys Val Pro Tyr Phe
                405                 410                 415
Tyr Arg Lys Lys Glu Lys Ile Glu Ser Ala Thr Leu Arg Val Pro
            420                 425                 430
Leu Val Ser Ile Tyr Ile Pro Ala Tyr Asn Cys Ser Lys Tyr Ile Val
        435                 440                 445
Arg Cys Val Glu Ser Ala Leu Asn Gln Thr Ile Thr Asp Leu Glu Val
    450                 455                 460
Cys Ile Cys Asp Asp Gly Ser Thr Asp Asp Thr Leu Arg Ile Leu Gln
465                 470                 475                 480
Glu His Tyr Ala Asn His Pro Arg Val Arg Phe Ile Ser Gln Lys Asn
                485                 490                 495
Lys Gly Ile Gly Ser Ala Ser Asn Thr Ala Val Arg Leu Cys Arg Gly
```

```
              500             505             510
Phe Tyr Ile Gly Gln Leu Asp Ser Asp Asp Phe Leu Glu Pro Asp Ala
            515                 520                 525

Val Glu Leu Cys Leu Asp Glu Phe Arg Lys Asp Leu Ser Leu Ala Cys
            530                 535                 540

Val Tyr Thr Thr Asn Arg Asn Ile Asp Arg Glu Gly Asn Leu Ile Ser
545                 550                 555                 560

Asn Gly Tyr Asn Trp Pro Ile Tyr Ser Arg Lys Leu Thr Ser Ala
            565                 570                 575

Met Ile Cys His His Phe Arg Met Phe Thr Ala Arg Ala Trp Asn Leu
            580                 585                 590

Thr Glu Gly Phe Asn Glu Ser Ile Ser Asn Ala Val Asp Tyr Asp Met
            595                 600                 605

Tyr Leu Lys Leu Ser Glu Val Gly Pro Phe Lys His Ile Asn Lys Ile
            610                 615                 620

Cys Tyr Asn Arg Val Leu His Gly Glu Asn Thr Ser Ile Lys Lys Leu
625                 630                 635                 640

Asp Ile Gln Lys Glu Asn His Phe Lys Val Val Asn Glu Ser Leu Ser
            645                 650                 655

Arg Leu Gly Ile Lys Lys Tyr Lys Tyr Ser Pro Leu Thr Asn Leu Asn
            660                 665                 670

Glu Cys Arg Lys Tyr Thr Trp Glu Lys Ile Glu Asn Asp Leu
            675                 680                 685

<210> SEQ ID NO 5
<211> LENGTH: 4968
<212> TYPE: DNA
<213> ORGANISM: Artificial sequence
<220> FEATURE:
<223> OTHER INFORMATION: cloning vehicles

<400> SEQUENCE: 5
acgttatcga ctgcacggtg caccaatgct tctggcgtca ggcagccatc ggaagctgtg      60
gtatggctgt gcaggtcgta aatcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattcatg tcccctatac taggttattg gaaaattaag ggccttgtgc     300
aacccactcg acttcttttg gaatatcttg aagaaaaata tgaagagcat ttgtatgagc     360
gcgatgaagg tgataaatgg cgaaacaaaa gtttgaatt gggtttggag tttcccaatc     420
ttccttatta tattgatggt gatgttaaat aacacagtc tatggccatc atacgttata     480
tagctgacaa gcacaacatg ttgggtggtt gtccaaaaga gcgtgcagag atttcaatgc     540
ttgaaggagc ggttttggat attagatacg gtgtttcgag aattgcatat agtaaagact     600
ttgaaactct caagttgat tttcttagca agctacctga aatgctgaaa atgttcgaag     660
atcgtttatg tcataaaaca tatttaaatg gtgatcatgt aacccatcct gacttcatgt     720
tgtatgacgc tcttgatgtt gttttataca tggacccaat gtgcctggat gcgttcccaa     780
aattagtttg ttttaaaaaa cgtattgaag ctatcccaca aattgataag tacttgaaat     840
ccagcaagta tatagcatgg cctttgcagg gctggcaagc cacgtttggt ggtggcgacc     900
atcctccaaa atcggatctg gttccgcgtg atccccgaa ttcccgggtc gactcgagcg     960
gccgcatcgt gactgactga cgatctgcct cgcgcgtttc ggtgatgacg gtgaaaacct    1020
ctgacacatg cagctcccgg agacggtcac agcttgtctg taagcggatg ccgggagcag    1080
```

```
acaagcccgt cagggcgcgt cagcgggtgt tggcgggtgt cggggcgcag ccatgaccca    1140
gtcacgtagc gatagcggag tgtataattc ttgaagacga aagggcctcg tgatacgcct    1200 attttatag gttaatgtca tgataataat ggtttcttag acgtcaggtg cacttttcg     1260 gggaaatgtg cgcggaaccc ctatttgttt atttttctaa atacattcaa atatgtatcc    1320
gctcatgaga caataaccct gataaatgct tcaataatat tgaaaaagga agagtatgag   1380
tattcaacat ttccgtgtcg cccttattcc cttttttgcg gcattttgcc ttcctgtttt    1440
tgctcaccca gaaacgctgg tgaaagtaaa agatgctgaa gatcagttgg gtgcacgagt   1500
gggttacatc gaactggatc tcaacagcgg taagatcctt gagagttttc gccccgaaga   1560
acgttttcca atgatgagca cttttaaagt tctgctatgt ggcgcggtat tatcccgtgt   1620
tgacgccggg caagagcaac tcggtcgccg catacactat tctcagaatg acttggttga   1680
gtactcacca gtcacagaaa agcatcttac ggatggcatg acagtaagag aattatgcag   1740
tgctgccata accatgagtg ataacactgc ggccaactta cttctgacaa cgatcggagg    1800
accgaaggag ctaaccgctt ttttgcacaa catgggggat catgtaactc gccttgatcg    1860
ttgggaaccg gagctgaatg aagccatacc aaacgacgag cgtgacacca cgatgcctgc    1920
agcaatggca acaacgttgc gcaaactatt aactggcgaa ctacttactc tagcttcccg    1980
gcaacaatta atagactgga tggaggcgga taaagttgca ggaccacttc tgcgctcggc   2040
ccttccggct ggctggttta ttgctgataa atctggagcc ggtgagcgtg gtctcgcgg    2100 tatcattgca gcactggggc cagatggtaa gccctcccgt atcgtagtta tctacacgac   2160
ggggagtcag gcaactatgg atgaacgaaa tagacagatc gctgagatag gtgcctcact   2220
gattaagcat tggtaactgt cagaccaagt ttactcatat atactttaga ttgatttaaa   2280
acttcatttt taatttaaaa ggatctaggt gaagatcctt tttgataatc tcatgaccaa   2340
aatcccttaa cgtgagtttt cgttccactg agcgtcagac cccgtagaaa agatcaaagg   2400
atcttcttga tccttttttt ttctgcgcgt aatctgctgc ttgcaaacaa aaaaaccacc   2460
gctaccagcg gtggtttgtt tgccggatca agagctacca actctttttc cgaaggtaac   2520
tggcttcagc agagcgcaga taccaaatac tgtccttcta gtgtagccgt agttaggcca   2580
ccacttcaag aactctgtag caccgcctac atacctcgct ctgctaatcc tgttaccagt   2640
ggctgctgcc agtggcgata gtcgtgtct taccggttg gactcaagac gatagttacc    2700
ggataaggcg cagcggtcgg gctgaacggg gggttcgtgc acacagccca gcttggagcg   2760
aacgacctac accgaactga gatacctaca gcgtgagcta tgagaaagcg ccacgcttcc   2820
cgaagggaga aaggcggaca ggtatccggt aagcggcagg gtcggaacag gagagcgcac   2880
gagggagctt ccagggggaa acgcctggta tctttatagt cctgtcgggt ttcgccacct   2940
ctgacttgag cgtcgatttt tgtgatgctc gtcagggggg cggagcctat ggaaaaacgc   3000
cagcaacgcg gccttttac ggttcctggc cttttgctgg ccttttgctc acatgttctt   3060
tcctgcgtta tcccctgatt ctgtggataa ccgtattacc gcctttgagt gagctgatac   3120
cgctcgccgc agccgaacga ccgagcgcag cgagtcagtg agcgaggaag cggaagagcg   3180
cctgatgcgg tattttctcc ttacgcatct gtgcggtatt tcacaccgca taaattccga   3240
caccatcgaa tggtgcaaaa cctttcgcgg tatggcatga tagcgcccgg aagagagtca   3300
attcagggtg gtgaatgtga aaccagtaac gttatacgat gtcgcagagt atgccggtgt   3360
ctcttatcag accgtttccc gcgtggtgaa ccaggccagc cacgtttctg cgaaaacgcg   3420
ggaaaaagtg gaagcggcga tggcggagct gaattacatt cccaaccgcg tggcacaaca   3480
```

```
actggcgggc aaacagtcgt tgctgattgg cgttgccacc tccagtctgg ccctgcacgc    3540
gccgtcgcaa attgtcgcgg cgattaaatc tcgcgccgat caactgggtg ccagcgtggt    3600
ggtgtcgatg gtagaacgaa gcggcgtcga agcctgtaaa gcggcggtgc acaatcttct    3660
cgcgcaacgc gtcagtgggc tgatcattaa ctatccgctg gatgaccagg atgccattgc    3720
tgtggaagct gcctgcacta atgttccggc gttatttctt gatgtctctg accagacacc    3780
catcaacagt attattttct cccatgaaga cggtacgcga ctgggcgtgg agcatctggt    3840
cgcattgggt caccagcaaa tcgcgctgtt agcgggccca ttaagttctg tctcggcgcg    3900
tctgcgtctg gctggctggc ataaatatct cactcgcaat caaattcagc cgatagcgga    3960 acggaaggc gactggagtg ccatgtccgg ttttcaacaa accatgcaaa tgctgaatga    4020
gggcatcgtt cccactgcga tgctggttgc caacgatcag atgcgctgg gcgcaatgcg    4080 cgccattacc gagtccggc tgcgcgttgg tgcggatatc tcggtagtgg gatacgacga    4140
taccgaagac agctcatgtt atatcccgcc gttaaccacc atcaaacagg attttcgcct    4200 gctgggcaa accagcgtgg accgcttgct gcaactctct cagggccagg cggtgaaggg    4260
caatcagctg ttgcccgtct cactggtgaa aagaaaaacc accctggcgc ccaatacgca    4320
aaccgcctct ccccgcgcgt tggccgattc attaatgcag ctggcacgac aggtttcccg    4380
actggaaagc gggcagtgag cgcaacgcaa ttaatgtgag ttagctcact cattaggcac    4440
cccaggcttt acactttatg cttccggctc gtatgttgtg tggaattgtg agcggataac    4500
aatttcacac aggaaacagc tatgaccatg attacggatt cactggccgt cgttttacaa    4560
cgtcgtgact gggaaaaccc tggcgttacc caacttaatc gccttgcagc acatccccct    4620
ttcgccagct ggcgtaatag cgaagaggcc cgcaccgatc gcccttccca acagttgcgc    4680
agcctgaatg gcgaatggcg ctttgcctgg tttccggcac cagaagcggt gccggaaagc    4740
tggctggagt gcgatcttcc tgaggccgat actgtcgtcg tccccctcaaa ctggcagatg    4800 cacggttacg atgcgcccat ctacaccaac gtaacctatc ccattacggt caatccgccg    4860
tttgttccca cggagaatcc gacgggttgt tactcgctca catttaatgt tgatgaaagc    4920
tggctacagg aaggccagac gcgaattatt tttgatggcg ttggaatt                 4968
```